United States Patent
Wang (10) Patent No.: US 10,219,934 B2
(45) Date of Patent: Mar. 5, 2019

(54) NASAL CAVITY DILATOR (71) Applicant: Lei Wang, Beijing (CN)

(72) Inventor: Lei Wang, Beijing (CN)

(*) Notice: Subject to any disclaimer, the term of this patent is extended or adjusted under 35 U.S.C. 154(b) by 110 days.

(21) Appl. No.: 15/516,385

(22) PCT Filed: Jun. 1, 2016

(86) PCT No.: PCT/CN2016/084306
§ 371 (c)(1),
(2) Date: Apr. 1, 2017

(87) PCT Pub. No.: WO2017/206104
PCT Pub. Date: Dec. 7, 2017

(65) Prior Publication Data
US 2018/0185187 A1 Jul. 5, 2018

(51) Int. Cl.
A61F 5/08 (2006.01)
A61M 29/02 (2006.01)

(52) U.S. Cl.
CPC .............. A61F 5/08 (2013.01); A61M 29/02 (2013.01)

(58) Field of Classification Search
CPC ........... A61F 5/08; A61F 13/126; A61F 5/56; A61M 29/02; A61M 16/0666; A61M 2025/0226
See application file for complete search history.

(56) References Cited

U.S. PATENT DOCUMENTS

D575,397 S    8/2008  Noce
2011/0118775 A1* 5/2011 Brown ............... A61F 5/08
                                                  606/199

FOREIGN PATENT DOCUMENTS

| EP | 0958798 A1 | 11/1999 |
| JP | 2014171789 A | 9/2014 |
| WO | WO0117468 A1 | 3/2001 |
| WO | WO2007119041 A1 | 10/2007 |
| WO | WO2012137182 A2 | 10/2012 |
| WO | WO2015051522 A1 | 4/2015 |
| WO | WO2015192162 A1 | 12/2015 |

* cited by examiner

Primary Examiner — Jocelin C Tanner
(74) Attorney, Agent, or Firm — Gokalp Bayramoglu (57) ABSTRACT The present invention provides a nasal dilator including: two intranasal stents (1) and a connecting band (2), wherein each of two ends of the connecting band (2) being symmetrically connected to one intranasal stent (1), each intranasal stent (1) having an elastic band-shape structure, each intranasal stent (1) has a straight-line shape, an arc-line shape, a bow shape, or a fold-line shape in a cross section perpendicular to a width direction of the elastic banded structure, each intranasal stent (1), along a length direction of the elastic band-shape structure, comprises: a nasal septum supporting section (3), a bending section (4), and a nasal alar dilating section (5), each intranasal stent (1) has a generally C-shape in a cross-section perpendicular to a central axis of nasal passages, wherein an opening of the C-shape faces towards a nasal base (11).

13 Claims, 5 Drawing Sheets

NASAL CAVITY DILATOR

CROSS REFERENCE TO RELATED APPLICATIONS

This application is the national phase entry of International Application No. PCT/CN2016/084306, filed on Jun. 1, 2016, the entire contents of which are incorporated herein by reference.

TECHNICAL FIELD

The present invention relates to the field of dilating device, especially to a nasal cavity dilator.

BACKGROUND

Currently, a considerable number of people are suffering from nasal obstruction disease (also known as rhinobyon). The narrowest part of the nasal cavity of the human body is the nasal valve area (intranasal hole). This nasal valve area is located in the deep part of the nasal vestibule and in front of the front-end of the inferior nasal concha. It is a long and narrow triangular region and is a part where the greatest nasal resistance exists. The nasal obstruction normally occurs in the nasal valve area and the front-end of the inferior nasal concha adjacent to the nasal valve area. Normally, the nasal obstruction is caused by the structural abnormalities, such as mucosa swelling, hyperplasia, hypertrophy, the nasal septum deviating, and the like. The nasal obstruction can cause breathing disorder, snoring and other symptoms.

The chronic and severe nasal passage obstructive symptoms described above are usually treated by surgery. However, the cost of the operation is usually high and cannot fundamentally cure the deformation of the nasal passage. Moreover, the removal of turbinate can cause "empty nose syndrome" and other sequelae, which will bring more pain to the patients.

Another solution to treat the nasal obstruction is using a nasal dilator. The vent ability of the nasal passages is improved by dilating the space of the nasal passages. An international patent application PCT/CN2013/085002 disclosed a nasal dilator. The nasal dilator includes two irregular annular intranasal stents and a U-shape connecting device. When the nasal dilator is arranged in the deep part of the nasal vestibule, the two irregular annular stents support and dilate the inner wall of the nasal alar near the nasal valve area (intranasal hole) from the inner side. Thus, the ventilation space of the nasal valve area and the front-end of the turbinate is dilated, thereby relieving the symptoms of nasal obstruction.

The intranasal stent of the existing nasal dilator can be divided into two types, i.e., columnar shape (or annular shape) intranasal stents and band shape intranasal stent. US published application U.S. Pat. No. D575,397 S1 discloses a columnar shape (or annular shape) intranasal stent. The advantage of the columnar shape (or annular shape) intranasal stent is its good expansion ability. The disadvantage of the columnar shape (or annular shape) intranasal stent is high air resistance and low adaptability to the nares of different shapes. The advantages of the band-shaped intranasal stent are comfortablity and high adaptability to the nares of different shapes. The disadvantage of the band-shaped intranasal stent is that the expansion strength in the two ends of the intranasal stent is insufficient.

SUMMARY OF THE INVENTION

The object of the present invention is to solve the technical problem existing in current nasal dilators, such as low expansion strength, low adaptability to nares of different shapes, and so on, which is caused by structural limitation. Provided is a nasal dilator, the intranasal stents of which have the advantages of both the band-shape intranasal stent and the columnar shape (or annular shape) intranasal stent. Therefore, the nasal dilator has the good dilating ability, ventilation ability, applicability, and comfortableness.

To achieve above objects, the present invention provides a nasal dilator. The nasal dilator comprises two intranasal stents and a connecting band. Each of two ends of the connecting band is symmetrically connected to one intranasal stent. Each intranasal stent has an elastic band-shape structure. Each intranasal stent has a straight-line shape, an arc-line shape, a bow shape, or a fold-line shape in a cross section perpendicular to a width direction of the elastic banded structure. Each intranasal stent, along a length direction of the elastic band-shape structure, comprises: a nasal septum supporting section on one side, a bending section in the middle, and a nasal alar dilating section on the other side. After being compressed, each intranasal stent is further bent and inserted into a nasal vestibule such that each intranasal stent has a generally C-shape in a cross-section perpendicular to a central axis of nasal passages. With a resilient force of each intranasal stent, a nasal septum is supported by the nasal septum supporting section and a nasal alar is dilated outwardly by being pushed by the nasal alar dilating section from the inside of a nasal cavity, wherein an opening of the C-shape faces towards a nasal base.

As a further improvement to the foregoing technical solution, each of the two intranasal stents is provided with a supporting arm for adjusting a resilient strength and a dilating strength of the intranasal stent in different positions. The supporting arm has the elastic band-shape structure. The supporting arm has a straight-line shape, an arc-line shape, a bow shape, or a fold-line shape in a cross section perpendicular to a width direction of the elastic band-shape structure. Two ends of the supporting arm are fixed to an inner side surface of the intranasal stent.

As a further improvement to the foregoing technical solution, each of the two intranasal stents is provided with at least two supporting arms. Each supporting arm has an elastic band-shape structure. The supporting arm has a straight-line shape, an arc-line shape, a bow shape, or a fold-line shape in a cross section perpendicular to a width direction of the elastic band-shape structure. Each supporting arm is used to adjust a resilient strength and a dilating strength of the intranasal stent in different positions. Two ends of one supporting arm are fixed to an inner side surface of the intranasal stent, and two ends of the remaining supporting arm are fixed to the inner side surface of the intranasal stent, or one end of the remaining supporting arm is fixed to the inner side surface of the intranasal stent and the other end of the remaining supporting arm is fixed to another supporting arm, or two ends of the remaining supporting arm are fixed to another supporting arm.

As a further improvement to the foregoing technical solution, two ends of the connecting band are connected to a side of the nasal septum supporting section that faces towards outside of a naris, or the two ends of the connecting band are connected to a side of the bending section that faces towards outside of the naris, or the two ends of the connecting band are connected to a side of the supporting arm that faces towards outside of the naris.

As a further improvement to the foregoing technical solution, each of a connection between the supporting arm and the intranasal stent and a connection between the connecting band and the intranasal stent is an integrated seamless connection, a plug-in connection, or an adhesive connection.

As a further improvement to the foregoing technical solution, each end of each intranasal stent is formed as a smooth hook structure.

As a further improvement to the foregoing technical solution, two ends of each intranasal stent are connected by a supporting arm such that each intranasal stent has an annular shape.

As a further improvement to the foregoing technical solution, the connecting band is a stripe-shape structure or a columnar structure that has a generally U-shape, C-shape, or V-shape.

As a further improvement to the foregoing technical solution, an angle formed by planes (i.e., plane perpendicular to the width direction of the intranasal stent) in which the intranasal stents are located respectively and orientated in an open direction of a U-shape of the connecting band is 90 degrees to 180 degrees.

The advantages of the nasal dilator of the present invention are:

1. Compared to the columnar shape (or annular shape) intranasal stent, the advantages of the present invention are as below:

a. Compared to the columnar shape (or annular shape) intranasal stent having a fixed perimeter, the intranasal stent of the present invention is designed to have an opening such that the size of the opening can be adjusted according to the sizes of the naris so as to fit different sizes and shapes of nares. Thus, the present invention has good adaptability, especially for those patients suffering from the deviation of the nasal septum and having a different size in left and right nares. The design of opening in the present invention can match the left and right intranasal stents with two nares of different sizes.

b. Under the same supporting strength, the intranasal stent of the present invention has a C-shape structure in a cross section perpendicular to the nasal passages and has a reduced cross section area compared to an O-shaped structure of the intranasal stent with columnar shape (or annular shape), better ventilation ability and comfortability.

2. Compared to the band-shaped intranasal stent, the advantages of the present invention are in that:

a. The resilient strength of the band-shaped intranasal stent is mainly applied to a portion of the nasal alar near the nasal dorsum (nasal bridge). The middle portion of the nasal alar and the part near the nasal alar groove lack support. The supporting arm provided by the present invention can provide support to each part of the nasal alar. This support arm is especially suitable for whites' long and narrow nares of which the nasal dorsum (nasal bridge) is positioned far from the nasal alar groove. In this situation, the supporting arm plays an important role to improve the dilating effect on the middle part of the nasal alar and the part near the nasal alar groove. The position, amount, and strength of the supporting arm can be adjusted flexibly, as needed. Hence, the present invention has a wider application range;

b. The intranasal stent and the supporting arm are mutually fixed and are not easy to deform after being inserted into the nasal cavity:

c. The design of the intranasal stent and the supporting arm is more flexible. For instance, for long and narrow nares, the intranasal stent may have a larger bending radian in a natural state such that it would be much easier for the user to insert the intranasal stent into the naris without feeling uncomfortable due to strong resilient strength. Because of the existence of the supporting arm, the intranasal stent keeps a necessary resilience in each position. The nasal dilator of the present invention avoids the following issue in common band-shape intranasal stents, i.e., the user's uncomfortable feelings due to a large resilient force near the nasal dorsum (nasal bridge) caused by a small radian of the intranasal stent or lack of resilient force due to the increase of radian:

d. Because of the existence of the supporting arm, the design to the elasticity of the intranasal stent is more efficient. Thus, the intranasal stent is thinner than the normal band-shape intranasal stent. Although the supporting arm is added, the air resistance of the whole structure almost equals to that of the band-shape structure.

3. If the connection design between the connecting band and the intranasal stent is the plug-in type, the intranasal stent and the connecting band can be replaced conveniently according to different shapes of the inner cavity of the nasal vestibular and nasal septum such that the scope of application of the nasal dilator is increased.

4. After the two intranasal stents are bent into a C-shape, an angle formed by planes in which the intranasal stents are located respectively and orientated in an open direction of a U-shape of the connecting band is 90 degrees to 180 degrees so as to ensure that the supporting strength of the intranasal stents fully acts on the nasal alar and an effective expansion is achieved.

The symbols of the drawings are described as below:
1. intranasal stent 2. connecting band 3. nasal septum supporting section
4. bending section 5. nasal alar dilating section 6. supporting arm
7. hook structure 8. nasal vestibule 9. nasal alar 10. nasal septum
11. nasal base 12. inner side surface of intranasal stent
13. nasal dorsum/nasal bridge

DETAILED DESCRIPTION OF THE INVENTION

The nasal dilator of the present invention will be illustrated in detail hereinafter by incorporating the drawings and the embodiments.

Figure 1:
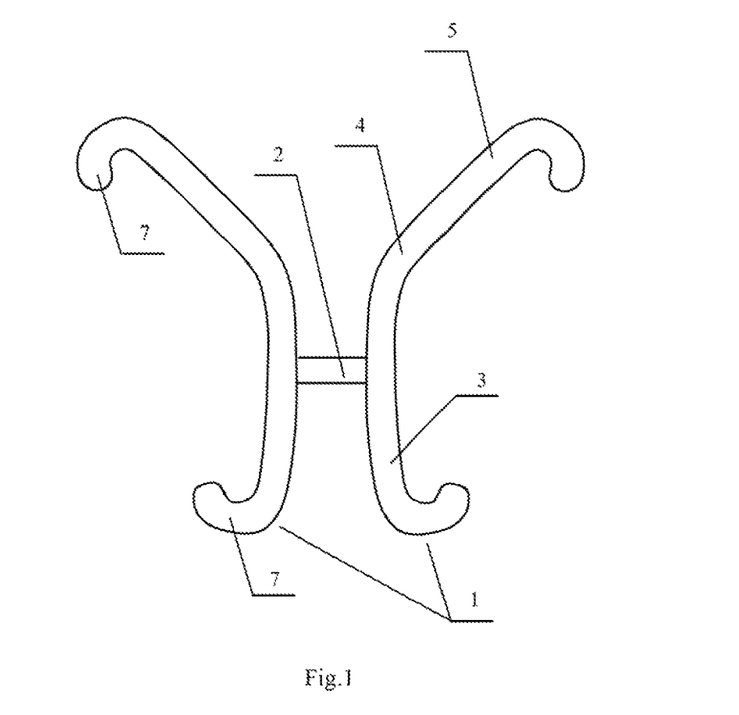
FIG. 1 is a structural schematic drawing of a nasal dilator in an embodiment of the present invention.

As shown in FIG. 1, the nasal dilator provided by the present invention includes two intranasal stents 1 and connecting band 2. Two intranasal stents 1 are symmetrically connected to two ends of connecting band 2 to form an integral whole. In use, two intranasal stents 1 are further bent respectively and then inserted into two nares of a user. The rebound ability of intranasal stents 1 is utilized to dilate passages of the nasal cavities near the nasal valve area so as to improve the efficiency of ventilation of the nasal cavities. Two ends of connecting band 2 enter the nasal cavities together with intranasal stents 1. A middle part of connecting band 2 is positioned across the nasal septum and exposed outside the nose. The user can remove the nasal dilator by pulling connecting band 2 outwardly.

Nasal stent 1 is made of elastic materials and has an irregular band-shape structure. Viewing in three dimensions, the overall characteristic of intranasal stent 1 is that after being stretched or flattened, one dimension (length) of intranasal stent 1 is the longest, one dimension (width) of intranasal stent 1 is the second longest, and one dimension (thickness) is the shortest or the thinnest. At this moment, nasal stent 1 has two largest surfaces, two second largest surfaces, and two smallest surfaces. In the natural state, the irregular band-shape structure has a straight-line shape, an arc shape, a bow shape, or a fold-line shape in a cross section perpendicular to the width direction of intranasal stent 1. That is to say, one of two largest surfaces can be curved or bent towards its normal direction to a certain degree along its length direction and become a curve. In addition, as shown in FIG. 2, the width and thickness of intranasal stent 1 can be different in different positions, wherein x, y, z represent the width direction, the length direction, and the thickness direction of intranasal stent 1, respectively.

Figure 3:
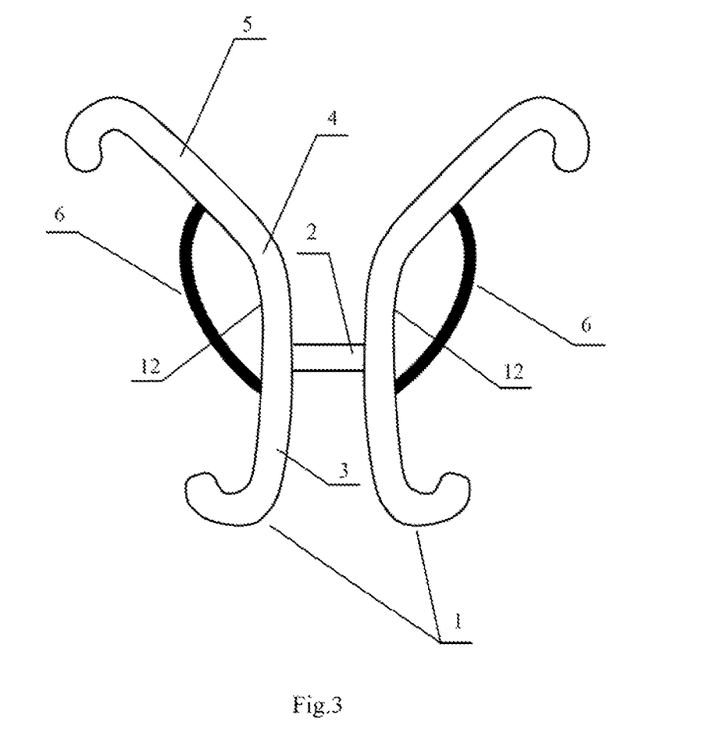
FIG. 3 is a structural schematic drawing of a nasal dilator in an embodiment of the present invention, in which the nasal dilator is provided with a supporting arm.
Figure 4:
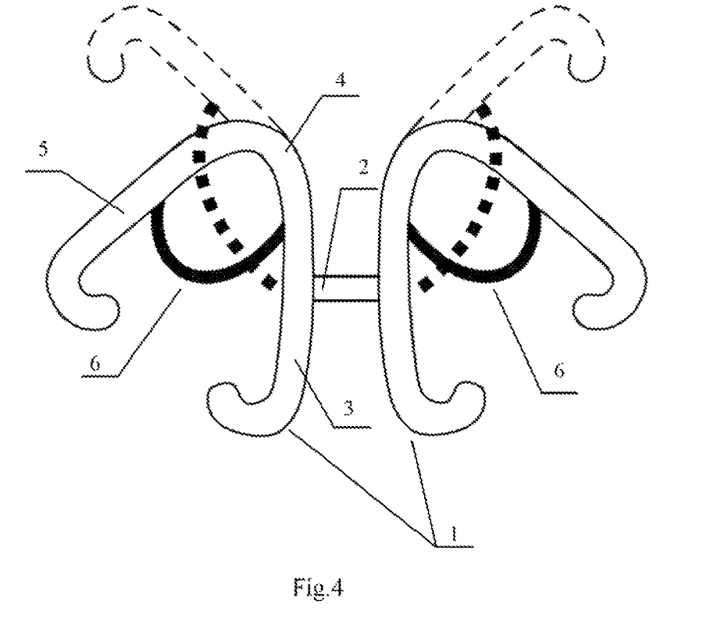
FIG. 4 is a state drawing of a nasal dilator illustrated in FIG. 3 where two intranasal stents of the nasal dilator are bent.
Figure 6:
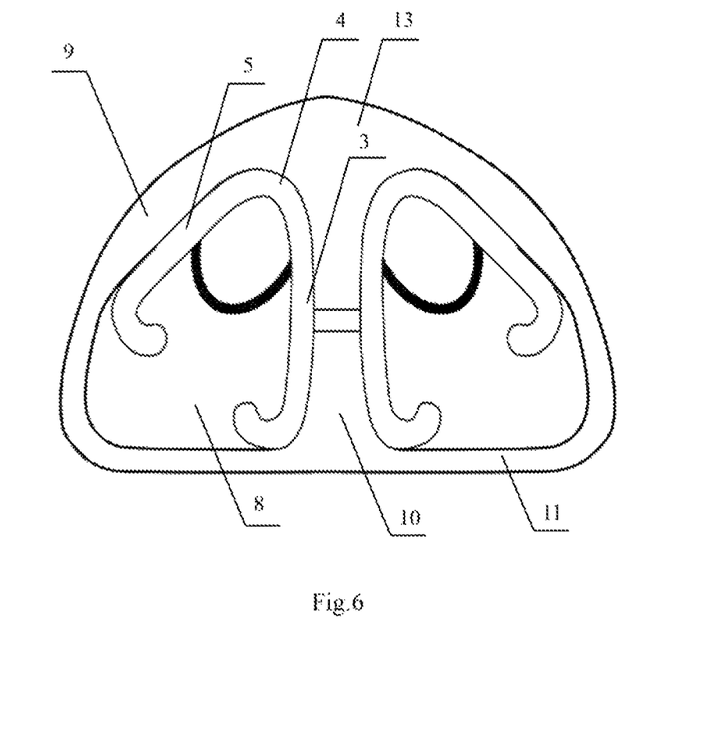
FIG. 6 is a state drawing of the nasal dilator illustrated in FIG. 3 where the nasal dilator is put into the nasal cavity.
Figure 7:
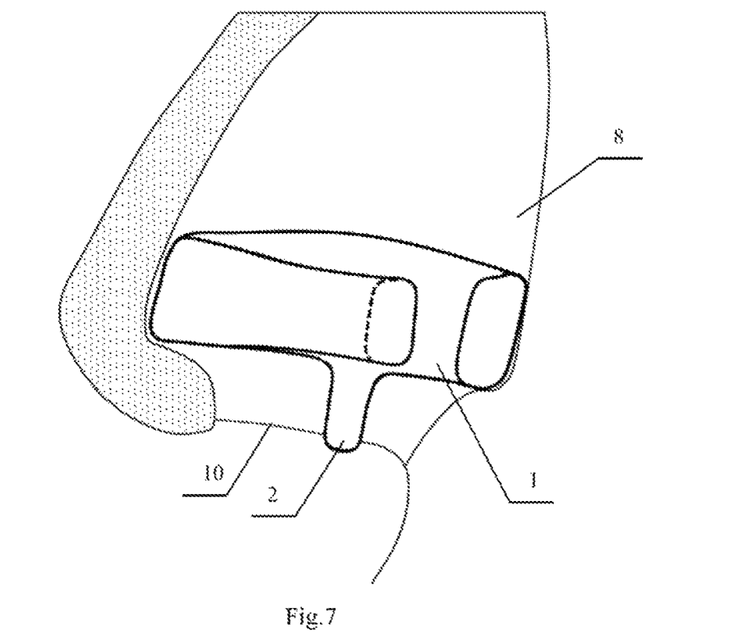
FIG. 7 is a side view of the nasal dilator illustrated in FIG. 6 where the nasal dilator is put into the nasal cavity.

Nasal stent 1 is the main part to support and dilate the nasal passage. As shown in FIG. 1, according to functionality, intranasal stent 1 is divided into three sections along the length direction of the band-shape structure. These sections are bending section 4 in the middle, nasal septum supporting section 3 on one side, and nasal alar dilating section 5 on the other side. In the natural state, the length directions of nasal septum supporting sections 3 of two intranasal stents are approximately parallel to each other. As shown in FIG. 3, two inner side surfaces 12 of intranasal stent faces towards two sides of the symmetry plane of two intranasal stents 1, respectively. When the user further bends intranasal stent 1 and inserts intranasal stent 1 into the nasal cavity, intranasal stent 1 has a shape of hair clasp, and now the most remarkable bending is occurred at bending section 4. A certain degree of bending and deformation may occur in nasal septum supporting section 3 and nasal alar dilating section 5, depending on different sizes and shapes of nares. As shown in FIG. 4, viewing from the cross-section perpendicular to the central axis of the nasal passages, the shape of the cross section of intranasal stent 1 is like a C-shape (also can be a U-shape, V-shape or bow shape, etc.), and now the width direction of intranasal stent 1 substantially parallels to the central axis of the nasal passages. The C-shape solid line is the presentation of a plane surrounded by the longest side and the shortest side of intranasal stent 1 being further bent. As shown in FIG. 6, in this situation, a middle part of the C-shape solid line is bending section 4, which is orientated towards the nasal bridge (nasal dorsum) of the user. On one side of the C-shape solid line is nasal septum supporting section 3, which is oriented towards the nasal septum of the naris. On the other side of the solid line is nasal alar dilating section 5, which is oriented towards the nasal alar of the naris. The gap of the C-shape faces towards nasal base 11 of the user. After the user put the nasal dilator in nasal vestibule 8, nasal septum 10 side of the nasal cavity is relatively fixed and nasal alar 9 side is easily movable. Therefore, intranasal stent 1 utilizes nasal septum 10 as the basic supporting surface, uses its resilience and nasal alar dilating section 5 to push nasal alar 9 outwardly so as to dilate the nasal passage. In this state, the largest surface of intranasal stent 1 abuts the inner wall of the nasal passage such that the nasal passages can be effectively supported, the pressure is dispersed in a reasonable way. Therefore, the user will feel more comfortable. The second largest surface of intranasal stent 1 faces towards the nasal passage. Since the second largest surface has an extremely small width (the thickness of intranasal stent 1), the resistance to the air is also very small.

In the nasal dilator with above structure, in order to meet the needs of the different shapes of noses, in natural state, where the nasal dilator haven't been inserted into the nasal cavity yet, the nasal dilator may have a straight-line shape, an arc shape, a bow shape, or a fold-line shape in a cross section perpendicular to the width direction of the nasal dilator (an angle of this cross section is equal to that of the appropriate C-shaped cross section described above).

Figure 2:
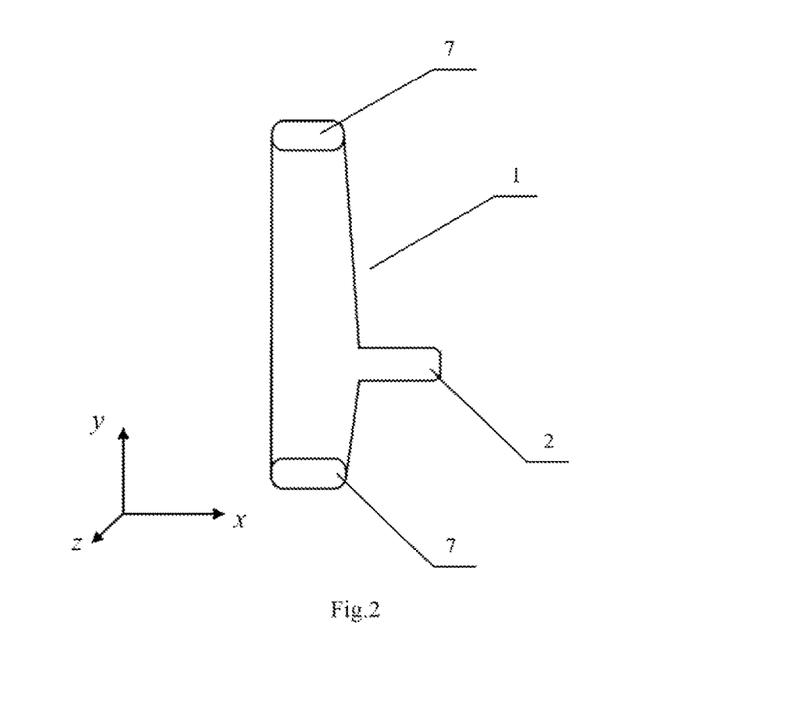
FIG. 2 is a side view of the nasal dilator illustrated in FIG. 1.

As shown in FIG. 1 and FIG. 2, to avoid two sharp ends of intranasal stent 1 inserted into the nasal cavity from making the user feel uncomfortable, these two ends can be slightly bent towards intranasal stent 1 inner side 12 to form smooth hook structure 7. Hence, after intranasal stent 1 is inserted into the nasal cavity, in the approximate C-shaped cross section described above, endpoints of two branches of the C-shape are slightly bent towards its center to prevent the end points from directly contacting with the nasal cavity. Therefore, the user will not feel uncomfortable. The bending radian and radius should not be very large so as to avoid bent hook structure 7 from forming an extra resistance to breathing.

Figure 5:
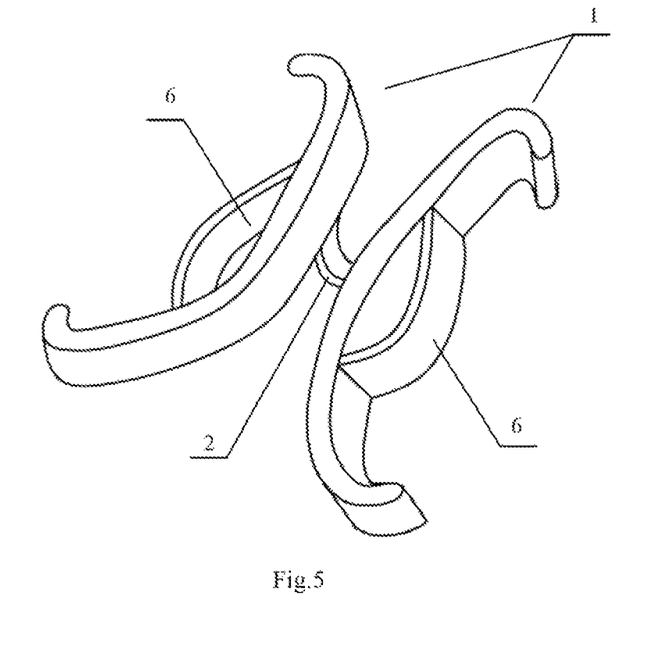
FIG. 5 is a perspective view of the nasal dilator illustrated in FIG. 3.
Figure 8:
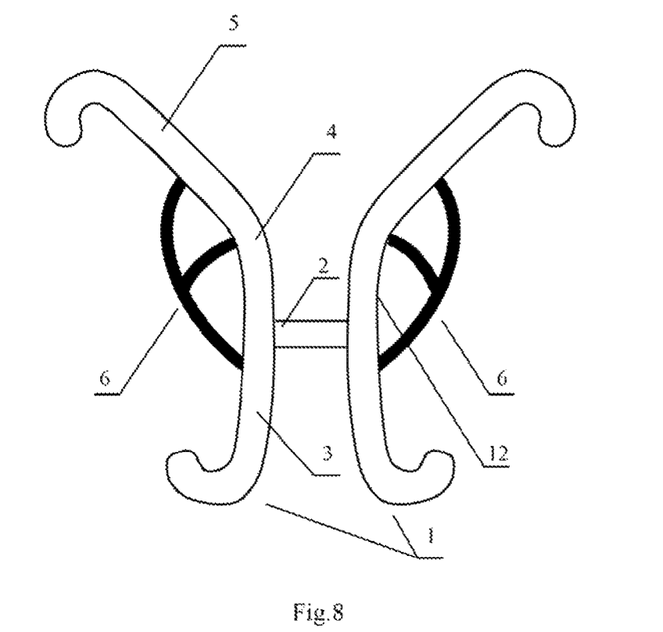
FIG. 8 is a structural schematic drawing of a nasal dilator in an embodiment of the present invention in which the nasal dilator is provided with two supporting arms.

In addition, as shown in FIG. 3, intranasal stent 1 is provided with supporting arm 6. The structure of supporting arm 6 is similar to that of intranasal stent 1 and is also an irregular band-shape structure. Supporting arm 6 is a core component used to strengthen the supporting force and the elastic force of intranasal stent 1. There may be one or more supporting arms 6. In the natural state, the width direction of supporting arm 6 is substantially consistent with the width direction of intranasal stent 1 where this supporting arm 6 is located. As shown in FIG. 3, FIG. 4, and FIG. 5, when there is one supporting arm 6, two ends of its band-shape structure are connected to inner side surface 12 of the intranasal stent along the length direction of supporting arm 6. When there are more than one supporting arms 6, two ends of each supporting arms 6 can be connected to inner side surface 12 of the intranasal stent. As shown in FIG. 8, for some supporting arms 6, one of the two ends may be connected to another supporting arms 6, and the other end of the two ends may be connecting with inner side surface 12 of the intranasal stent, or both of the two ends may be connected to other supporting arms 6. In a particular situation, the width of the supporting arm may be longer than the length of the supporting arm.

In the natural state, the supporting arm may have a straight-line shape, an arc shape, a bow shape, a fold-line shape, or the like in a cross section perpendicular to the width direction of the supporting arm.

As shown in FIG. 4, when the user further bends intranasal stent 1 and inserts it into naris, viewing from a cross-section perpendicular to the central axis of the nasal passages, the supporting arm may be bent, stretched, compressed, or have another kind of deformation. The width direction of supporting arm 6 is substantially parallel to the central axis of the nasal passages, such that the second largest surface of the intranasal stent faces towards the nasal passages. Since supporting arm 6 is extremely thin, the extra resistance to breathing is small. In this situation, supporting arm 6 uses its rebound ability to provide an extra elastic force for bending section 4 of intranasal stent 1 and provides an extra supporting force for nasal septum supporting section 3 and nasal alar dilating section 5, so as to optimize the rebound efficiency of intranasal stent 1.

Based on above structure of the nasal dilator, the connecting position between two ends of supporting arm 6 and intranasal stent 1 can be adjusted along the length direction of the intranasal stent to achieve the different supporting effect. The width and length of supporting arm 6 can be different from that of intranasal stent 1

As shown in FIG. 1, two ends of connecting band 2 are symmetrically connected to the second largest surfaces of two intranasal stents 1 that face towards outside of the nose, respectively. The particular connecting position may be on nasal septum supporting section 3 or bending section 4 or on a surface of a certain supporting arm that faces towards outside of the nose. In this embodiment, connecting band 2 is connected to the second largest surface of bending section 4 that faces towards outside of the nose.

Figure 9:
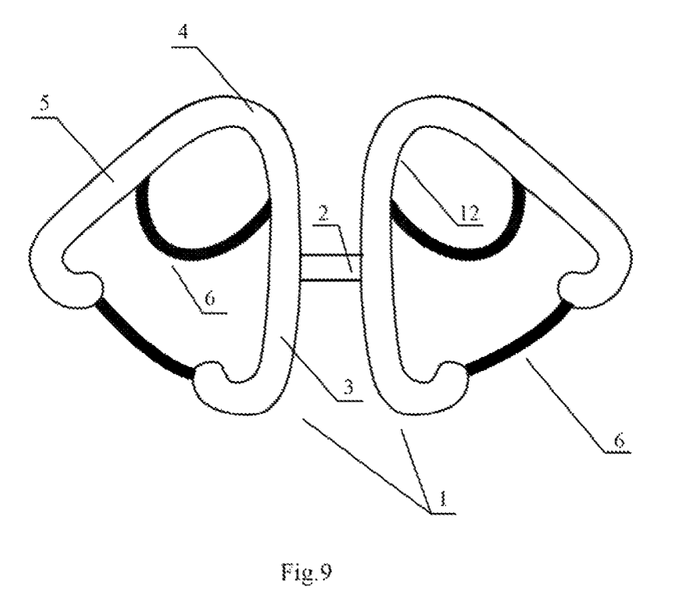
FIG. 9 is a structural schematic drawing of another nasal dilator in an embodiment of the present invention in which the nasal dilator is provided with two supporting arms.

In addition, as shown in FIG. 9, two ends of each of two intranasal stents 1 may be connected by supporting arm 6 such that intranasal stent 1 has an annular shape.

Figure 10:
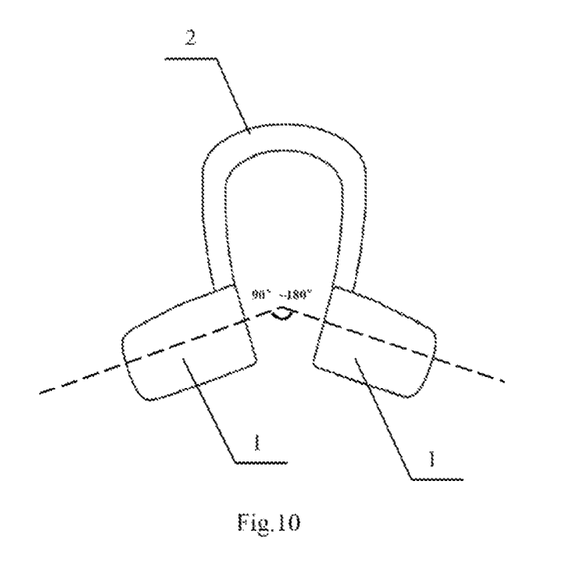
FIG. 10 is a drawing showing the location relationship between the two intranasal stents in an embodiment of the present invention.

As shown in FIG. 2, the connection between connecting band 2 and intranasal stent 1 may be integrated seamless connection, plug-in connection, or adhesive connection. Above three types of connections are also available for the connection between the supporting arms and the intranasal stents. The connecting band can be an irregular band-shape structure or columnar structure. As shown in FIG. 10, in a natural state, in a cross section that passes through two ends and the central point of the connecting band, the connecting band may have a U-shape, C-shape, V-shape or arched shape, etc. In addition, an angle formed by planes (i.e., plane perpendicular to the width direction of the intranasal stent), in which two intranasal stents are located respectively and orientated in the open direction of the U-shape connecting band, is 90 degrees to 180 degrees, so as to ensure that the supporting strength of intranasal stents 1 fully acts on the nasal alar and an effective expansion is achieved.

Finally, it should be noted that the embodiments described above are only to explain the technical solutions of the present invention, but not to limit the present invention. Although the present invention is described by referring to the embodiments, those skilled in the art should understand that modifications and equivalents do not depart from the spirit and scope of the technical solutions of the present invention, and should fall within the protective scope of the present invention.

What is claimed is:
1. A nasal dilator, wherein the nasal dilator comprises:
two intranasal stents; and
a connecting band,
wherein
each of two ends of the connecting band is symmetrically connected to one intranasal stent,
each intranasal stent has an elastic band-shape structure,
said each intranasal stent has a straight-line shape, an arc-line shape, a bow shape, or a fold-line shape in a cross section perpendicular to a width direction of the elastic band-shape structure,
said each intranasal stent, along a length direction of the elastic band-shape structure, comprises: a nasal septum supporting section on one side, a bending section in the middle, and a nasal alar dilating section on an other side,
after being compressed, said each intranasal stent is further bent and inserted into a nasal vestibule such that said each intranasal stent has a C-shape in a cross-section perpendicular to a central axis of nasal passages,
with a resilient force of said each intranasal stent, a nasal septum is adapted to be supported by the nasal septum supporting section and a nasal alar is adapted to be dilated outwardly by being pushed by the nasal alar dilating section from inside of a nasal cavity, wherein an opening of the C-shape faces towards a nasal base; and wherein each end of said each intranasal stent is formed as a smooth hook structure.

2. The nasal dilator of claim 1, wherein said each intranasal stent is provided with a supporting arm for adjusting a resilient strength and a dilating strength of the intranasal stent in different positions, the supporting arm has the elastic band-shape structure, the supporting arm has a straight-line shape, an arc-line shape, a bow shape, or a fold-line shape in a cross section perpendicular to a width direction of the elastic band-shape structure, two ends of the supporting arm are fixed to an inner side surface of said each intranasal stent.

3. The nasal dilator of claim 2, wherein the two ends of the connecting band are connected to a side of the nasal septum supporting section that faces towards outside of a naris, or the two ends of the connecting band are connected to a side of the bending section that faces towards outside of the naris, or the two ends of the connecting band are connected to a side of the supporting arm that faces towards outside of the naris.

4. The nasal dilator of claim 3, wherein each of a connection between the supporting arm and the intranasal stent and a connection between the connecting band and the intranasal stent is an integrated seamless connection, a plug-in connection, or an adhesive connection.

5. The nasal dilator of claim 2, wherein two ends of said each intranasal stent are connected by the supporting arm such that said each intranasal stent has an annular shape.

6. The nasal dilator of claim 1, wherein said each intranasal stent is provided with at least two supporting arms, each supporting arm has an elastic band-shape structure, each supporting arm has the elastic band-shape structure, the at least two supporting arms have a straight-line shape, an arc-line shape, a bow shape, or a fold-line shape in a cross section perpendicular to a width direction of the elastic band-shape structure, each supporting arm is used to adjust a resilient strength and a dilating strength of the intranasal stent in different positions,
wherein two ends of one supporting arm are fixed to an inner side surface of the intranasal stent, and two ends of the remaining supporting arm are fixed to the inner side surface of the intranasal stent, or one end of the remaining supporting arm is fixed to the inner side surface of the intranasal stent and the other end of the remaining supporting arm is fixed to another supporting arm, or two ends of the remaining supporting arm are fixed to another supporting arm.

7. The nasal dilator of claim 6, wherein two ends of said each intranasal stent are connected by the supporting arm such that said each intranasal stent has an annular shape.

8. The nasal dilator of claim 6, wherein said two ends of the connecting band are connected to a side of the nasal septum supporting section that faces towards outside of a naris, or the two ends of the connecting band are connected to a side of the bending section that faces towards outside of the naris, or the two ends of the connecting band are connected to a side of each supporting arm that faces towards outside of the naris.

9. The nasal dilator of claim 8, wherein each of a connection between the supporting arm and the intranasal stent and a connection between the connecting band and the intranasal stent is an integrated seamless connection, a plug-in connection, or an adhesive connection.

10. The nasal dilator of claim 1, wherein two ends of said each intranasal stent are connected by a supporting arm such that said each intranasal stent has an annular shape.

11. The nasal dilator of claim 1, wherein the connecting band is a stripe-shape structure or a columnar structure that has a U-shape, C-shape, or V-shape.

12. The nasal dilator of claim 1, wherein an angle formed by planes in which the intranasal stents are located respectively and orientated in an open direction of a U-shape of the connecting band is 90 degrees to 180 degrees.

13. The nasal dilator of claim 1, wherein two ends of said each intranasal stent are connected by a supporting arm such that said each intranasal stent has an annular shape.

\* \* \* \* \*